United States Patent [19]

Desmonts et al.

[11] Patent Number: 4,612,281
[45] Date of Patent: Sep. 16, 1986

[54] IMMUNOASSAY FOR DETECTING IMMUNOGLOBULINS AND TEST KIT

[75] Inventors: Georges Desmonts, Paris, France; Jack S. Remington, Menlo Park, Calif.

[73] Assignee: Palo Alto Medical Foundation Research Institute, Palo Alto, Calif.

[21] Appl. No.: 439,433

[22] Filed: Nov. 5, 1982

Related U.S. Application Data

[63] Continuation-in-part of Ser. No. 212,535, Dec. 3, 1980, abandoned.

[51] Int. Cl.⁴ ..................... G01N 33/53; G01N 33/569
[52] U.S. Cl. ........................................... 435/7; 435/34; 435/810; 436/513; 436/518; 436/519; 436/534; 436/805; 436/808; 436/811
[58] Field of Search ......................... 424/11, 85, 88; 436/518, 528, 534, 541, 811, 513, 519, 805, 808; 435/7, 34, 810

[56] References Cited

U.S. PATENT DOCUMENTS

| | | | |
|---|---|---|---|
| 3,415,361 | 12/1968 | Chambliss | 436/531 |
| 3,562,384 | 2/1971 | Arquilla | 436/519 X |
| 3,853,467 | 11/1974 | Giaever | 436/805 |
| 3,904,367 | 9/1975 | Galikersuch | 436/805 |
| 3,979,184 | 9/1976 | Giaever | 436/525 |
| 3,979,509 | 9/1976 | Giaever | 436/525 |
| 4,041,146 | 8/1977 | Giaever | 436/525 |
| 4,092,116 | 5/1978 | Giaever | 435/23 |
| 4,115,543 | 9/1978 | Wallace | 436/519 X |
| 4,169,138 | 9/1979 | Jonsson | 436/519 X |
| 4,189,466 | 2/1980 | Ainis | 436/519 X |
| 4,292,403 | 9/1981 | Duermeyer | 435/5 |
| 4,297,004 | 10/1981 | Claude | 436/513 |
| 4,407,943 | 10/1983 | Cole et al. | 436/528 |

OTHER PUBLICATIONS

A. F. Bradburne et al., Journal of General Virology, 44, part 3, 615–623 (1979).
Palmer et al., Serodiagnosis of Toxoplasmosis, Rubella, Cytomegalic Inclusion Disease, Herpes Simplex, U.S. Dept. HEW PITS Center for Dis. Control, Atlanta, Ga., 1/74, pp. 24–37.
Desmont, "Direct Agglutination Test", J. Clin. Micro., 6/80, vol. 9, No. 6, pp. 562–568.
Desmont et al., "Immunoglobulin M-Immunosorbent Assay", J. Clin. Micro., 81, pp. 486–491, vol. 14, #5.

Primary Examiner—Sidney Marantz
Attorney, Agent, or Firm—Ciotti & Murashige

[57] ABSTRACT

An immunoassay for detecting disease associated Ig, such as IgM associated with acute forms of *Toxoplasma gondii* infection. Wells of microtiter plates are first coated with an antibody against the Ig to be detected and the test sample, e.g. serum, is then added and incubated. After removal of non-adsorbed materials from the wells, an insoluble visible form of the cognate antigen to the Ig, such as antigen fixed to latex particles, is added. If no such Ig is present in the sample, the antigen will appear as a smooth button on the bottom of the well; whereas if such Ig is present in significant quantity, the antigen will be captured by adsorbed antiIg-Ig complexes and distributed on the wall of the well according to the distribution of the antiIg-Ig complex thereon.

22 Claims, No Drawings

IMMUNOASSAY FOR DETECTING IMMUNOGLOBULINS AND TEST KIT

CROSS-REFERENCE TO RELATED APPLICATION

This application is a continuation-in-part of U.S. copending Ser. No. 212,535, filed Dec. 3, 1980, abandoned.

DESCRIPTION

1. Technical Field

The invention concerns an immunoassay for detecting immunoglobulin (Ig) against a given antigen. The invention is particularly adapted to detecting IgM that is associated with acute forms of Toxoplasma infection.

2. Background Art

Several techniques have been used previously to serodiagnose Toxoplasma infection by detecting antibodies against Toxoplasma antigen. Among these tests are the direct agglutination test (DA) and the IgM-ELISA test. The DA test and improvements thereon are discussed by Desmonts, G. and Remington, J. S., Direct Agglutination Test for Diagnosis of Toxoplasma Infection: Method for Increasing Sensitivity and Specificity, J Clin Microbiology, Vol. 11, No. 6, p 562–568, June 1980. The DA involves adding whole organisms or antigen-coated carrier particles to various dilutions of serum in the wells of a microtiter plate and determining visually whether agglutination has occurred. "Agglutination" refers to the phenomenon that occurs when the serum contains significant amounts of antitoxoplasma Ig. It involves multiple interactions between antigenic sites on the organisms' or carrier particles' surfaces and the antitoxoplasma Ig that cause the organisms or coated carrier particles to coalesce into a matrix or network in which the individual organisms or particles are interconnected by the Ig. The network settles out of the liquid phase as a mat-like layer over the wetted wall of the well. If the serum contains no or insignificant amounts of antitoxoplasma Ig, no network is formed and the individual organisms or coated carrier particles settle into a smooth button in the well bottom. Thus, a smooth button of organisms or particles in the bottom of a well is a completely negative reading, whereas a uniform layer of coalesced organisms or antigen-coated carrier particles over the wetted wall of a well is a definitely positive reading. Intermediate readings (some layer formation, some button formation) indicate the presence of varying amounts of antitoxoplasma Ig in the serum. Quantitative extrapolations of these readings may be made by correlating them to readings made on standard sera. Advantages of the DA are that it uses inexpensive reagents, is simple, and is read easily. Its disadvantages are that it lacks specificity and sensitivity, and is subject to the prozone phenomenon. Another serious disadvantage of the DA is that it gives false positives due to "naturally occurring" antibody. In order to avoid false positives, 2-mercaptoethanol must be used in the test which negates its use for detecting IgM.

The IgM-ELISA (enzyme-linked immunosorbent assay) and variations thereof are described in U.S. Pat. No. 4,292,403. It is a double sandwich assay in which an immunosorbent surface, such as the well of a microtiter plate, is first coated with antihuman IgM. A sample is then applied to the surface and any antitoxoplasma IgM in the sample will bind to the antihuman IgM coating. A solution of Toxoplasma gondii antigen is then applied followed by application of a solution of labeled antitoxoplasma Ig (or labeled antigen binding fragment). Presence of the labeled antibody (and thus any antitoxoplasma IgM in the sample) is detected by treating the surface with an enzyme substrate and reading the surface spectrophtometrically. The advantages of the IgM-ELISA relative to the DA is that it detects a specific Ig class and is more sensitive. However, it requires expensive labeled reagents, involves more steps, and has a more demanding reading phase.

The present invention provides an assay that is different from the DA and IgM-ELISA in that it is not based on agglutination or reagents labeled with enzymatic, fluorescent or radioactive molecules but possesses the advantages of both assays without their principal drawbacks. In this regard, the invention assay may be used to detect specific Ig classes with relatively inexpensive reagents and a simple visual reading phase.

DISCLOSURE OF THE INVENTION

One aspect of the invention is an immuno-assay for detecting an Ig against a specific antigen in a sample of body fluid comprising the steps of:
  (a) adsorbing an antibody against said Ig onto a solid surface;
  (b) applying the sample to the adsorbed antibody against said Ig and incubating the resulting mixture;
  (c) separating the nonadsorbed fraction from the adsorbed fraction of the incubated mixture of step (b);
  (d) applying an insoluble, nontranslucent, i.e. opaque, form of the antigen to the adsorbed fraction; and
  (e) observing the extent to which the insoluble antigen is bound to the adsorbed fraction.

As applied to detecting IgM associated with an acute form of Toxoplasma infection in a sample of human body fluid the assay involves the steps of:
  (a) adsorbing antihuman IgM antibody onto a solid surface;
  (b) applying the sample to the adsorbed antihuman IgM antibody and incubating the resulting mixture;
  (c) separating the nonadsorbed fraction from the adsorbed fraction of the incubated mixture of step (b);
  (d) applying an insoluble form of Toxoplasma gondii antigen to the adsorbed fraction at a basic pH and incubating the resulting mixture; and
  (e) observing the extent to which the antigen is bound to the adsorbed fraction.

Another aspect of the invention is a test kit for carrying out the above-described assay comprising in association:
  (a) an antibody against the Ig; and
  (b) an insoluble, nontranslucent, i.e. opaque, form of the antigen.

Modes for Carrying Out the Invention

The invention assay involves the capture of an insoluble form of an antigen by an antiIg-Ig complex that is immobilized by fixation to a solid surface. Thus, unlike the above described prior art tests neither reaction species in the final incubation is in solution. Instead, the antiIg-Ig complex and the antigen are both solid phase, the former being in the form of a layer fixed to a solid surface and the latter being fixed on the surface of an insoluble particle such as a whole organism or a natural or synthetic carrier.

The immunoassay of the invention is particularly useful for serodiagnosing congenital (neonatal and perinatal) and postnatal acute forms of toxoplasmosis and Toxoplasma infection that afflict humans and the following disclosure relates to embodiments of the assay that is used to detect IgM associated with such conditions.

Antitoxoplasma IgM associated with acute forms of this infection are believed to occur in most, if not all, of the body fluids including the serum, peritoneal fluid, urine, saliva, vaginal fluid, cerebrospinal fluid, and amniotic fluid. Because of their ease of collection, blood serum is preferred in serodiagnosing postnatal forms of the infection whereas amniotic fluid, umbilical cord blood, or serum are preferred for diagnosing congenital forms.

In the initial step of the acute toxoplasmosis immunoassay a layer of antihuman IgM antibody is adsorbed onto a solid surface. The serum of any of the various nonhuman species of the Animalia kingdom may be used as the source of antibody against human IgM. The antibody should have a high capacity for specific binding with human IgM. This capacity may be confirmed using the IgM-IFA test, immunoelectrophoresis or ELISA. Preferably the antihuman IgM antibody is applied to the surface in dilute form (eg, aqueous solution) under pH, time, and temperature conditions that maximize its adsorption to the surface. Preferably it is applied at about 4° to 6° C. at a pH of about 9.8 to 9.9 and permitted to incubate under these conditions for 18 to 24 hr. Microtiter plates or glass slides that are commercially available provide excellent immunosorbent surfaces onto which the layer of antihuman IgM antibody may be adsorbed. Microtiter plates have a plurality of wells or depressions into which the antibody solution may be placed and are typically made from materials that are chemically inert to the reagents commonly used in immunoassays. Such materials include polystyrene, polyolefins such as polypropylene and polyethylene, chlorinated polyolefins such as polyvinylchloride, polyesters such as polyethylene terephthalate, polyamides, and polyurethanes. After an appropriate incubation period excess antihuman IgM antibody preparation is drained off or otherwise removed from the surface and the surface is washed, such as with phosphate buffered saline (PBS) containing a small amount of a nonionic surfactant, to clear the surface of any nonadsorbed materials. In order to ensure that the plate surface is entirely coated the wash may be followed with a post-coat of albumin, bovine serum, or similar protein.

The sample is then applied to the adsorbed layer of antihuman IgM antibody and left in contact therewith to incubate. The sample may be freshly acquired or taken from storage. If the sample is stored, it should be kept under conditions that preserve its reactivity. In general body fluids may be frozen and kept for prolonged periods at temperatures below about −20° C. and still be useable in the invention assay. The time and temperature conditions under which the sample is incubated in contact with the adsorbed layer of antihuman IgM antibody preferably optimize the likelihood of stable binding between the adsorbed antihuman IgM antibody and any IgM present in the sample fluid. Temperatures of about 30° to 37° C. and incubation times of 1 to 2 hr generally permit good binding.

After incubation with the sample, that portion of the sample which has not bound to the antihuman IgM antibody fixed to the surface is drained from the surface and the surface is washed to remove any nonadsorbed materials that were not eliminated by draining. After washing the nonadsorbed fraction of the sample from the surface of the well *Toxoplasma gondii* antigen in an insoluble form is applied to the surface. By "insoluble" it is meant that the antigen is not added as a solution and does not go into solution under the conditions of its application. Instead, the antigen is fixed on the surface of a nontranslucent, insoluble particle. Insoluble forms of *Toxoplasma gondii* antigen include whole organisms such as are used in the DA test and whose preparation is described by Desmonts and Remington, supra, and antigen that is fixed chemically or physically to an insoluble, nontranslucent natural or synthetic support or carrier but is still capable of specific binding to antitoxoplasma IgM. Inert supports and carriers that are conventionally used in indirect or passive agglutination immunoassays, such as red blood cells, latex, bentonite and other clays, and available immunosorbent beads made of activated cross-linked dextran, agarose, glass, polystyrene, or polyacrylamide may be used.

Antigen on the particles will bind to the antitoxoplasma IgM component of the antihuman IgM antibody-antitoxoplasma IgM complexes bound to the solid surface thus "capturing" the particle on the surface at the complex site. The presence of the captured particles on the surface may be observed visually or by optical instrument because they are nontranslucent (ie, they have optical characteristics such as opacity and/or color that enable them to be detected optically). When the immune complexes are immobilized on a well-shaped surface, such as on the wells of microtiter plates, antigen-bearing particles that are not captured will settle by gravitation into the bottom of the well. Thus, in an assay of a sample that contains no antitoxoplasma IgM, none of the antigen-bearing particles will be captured on the well walls and they will settle to the bottom of the well. In the case of positive samples, capture of the particles will occur and the antigen particles will be distributed over the complex-coated surface of the well. The distribution pattern of captured antigen-bearing particles is similar to the distribution pattern of agglutinated antigen that occurs in the DA and the same reading criteria as are used in the DA (Desmonts and Remington, supra, p 564) may be used to distinguish positive (a uniform mat-like distribution) and negative (a button distribution) distribution patterns.

The antigen-bearing particles are applied to the surface at a basic pH, preferably about 8.2 to 8.7. Such conditions may be achieved by applying the antigen-coated particles suspended in an appropriate alkaline buffer. Acid pHs should be avoided since spontaneous agglutination occurs when the pH is acid. It has been found that the antigen concentration, at least when whole organisms are used, affects the test results and that concentrations of about 3.3 to $3.5 \times 10^7$ organisms/ml give the best results. The test results may also be affected by temperature. Incubation of the antigen in the cold (4° C.) may give false-positive results. Therefore, incubation at about 35°–40° C. is recommended. Care should be taken to prevent drying of the antigen on the surface of the carrier. The reaction may be read after about 14 to 18 hrs (or longer as long as the reagents have not dried).

The following examples further illustrate the use of the invention test to detect the presence of antitoxoplasma IgM associated with acute forms of Toxoplasma infection and a comparison of this test with prior art tests. The materials and procedures used in Examples 1 through 6 were as follows.

Antigen Preparation. Purified Toxoplasma organisms are tachyzoites of the RH strain of *Toxoplsma gondii*. Tachyzoites were obtained either as described by Desmonts and Remington, supra, or from peritoneal exudates of mice infected two days earlier.

Prior Art Tests. The Sabin-Feldman dye test (DT) (Remington, J S, Desmonts, G, toxoplasmosis, in Remington, J R, and Klein, J O (eds), *Infectious Diseases of the Fetus and Newborn Infant*, Philadelphia, W B Saunders Company, 1976, pp 191-332; Handman, E, Remington, J S, Serological and immunochemical characterization of monoclonal antibodies to *Toxoplasma gondii*, *Immunology*, 40: 579-88, 1980), the Toxoplasma IgM-IFA test (Welch, P C, Masur, H, Jones T C, Remington, J S, The serological diagnosis of acute lymphadenopathic toxoplasmosis, *J Infect Dis*, 142:156-64, 1980), and the IgM-ELISA test (Remington, J S, et al, *J Pediatrics*, 98: 32-36, 1981 and U.S. patent application Ser. No. 194,682) were used.

Rheumatoid factor (RF) titers were determined by the latex agglutination method (Rapi/Tex RF kit, Behring Diagnostics, American Hoechst Corp, Somerville, N.J.). Fluorescent ANA (FANA) titers were determined by immunofluorescence.

Antihuman IgM Antibody. Rabbit antihuman IgM serum or the IgG fraction thereof ($\mu$-chain specific) may be obtained from any commercial source. In the experiments described in this application antiserum to human IgM was obtained from Cappell Laboratories (Cochranville, Penna.). The specific binding of human IgM by this antiserum was tested and confirmed by the IgM-IFA test.

Human Sera. The characteristics of the sera are described in the examples below.

A serum sample obtained from a patient one month after clinical onset of acute toxoplasmosis and that had a positive titer of 1:16384 in the DT and positive titers of 1:1280 in the IgM-IFA test and 1:16384 in the IgM-ELISA test served as positive control.

A pool of seven sera obtained from healthy individuals which were negative in the Toxoplasma DT, IgM-IFA, and IgM-ELISA as well as negative for RF and FANA served as negative control.

The Invention Method. Wells of disposable, U-shaped, rigid polystyrene microtiter plates (Dynatech Laboratories, Inc) were coated with 100 $\mu$l of the IgG fraction of rabbit antihuman IgM ($\mu$-chain specific) serum, diluted 1:3000 in 0.1M carbonate buffer, pH 9.8. After overnight incubation at 4° C. the plates were washed three times for 5 min each in phosphate buffered saline (PBS) containing 0.05% Tween 20 nonionic surfactant (PBS-T). Plates were postcoated with 1% bovine serum albumin (BSA) in PBS-T for 1 hr at 37° C. and washed again. Aliquots of 150 $\mu$l of serum dilutions in PBS (sera were diluted four-fold beginning with a dilution of 1:16) were added to the washed wells and the plates were incubated for 1 hr at 37° C. and then washed twice in PBS-T and twice in PBS. Suspensions of Toxoplasma antigen were diluted in alkaline buffer pH 8.2-8.7 to concentrations of 3.3-3.5 × 10$^7$ organisms/ml. Fifty $\mu$l of these suspensions were added to each well and the plates were incubated overnight at 37° C. The organism distribution patterns were recorded from 0 to +3 and the titers expressed as the highest serum dilution exhibiting definitely +3 pattern. In each test a positive and negative control were included.

EXAMPLE 1

Twenty-five sera obtained from uninfected individuals that were sero-negative in the DT were tested using the invention method. Negative results were obtained for all 25 sera.

EXAMPLE 2

Twenty-five sera positive in the DT and negative in the IgM-IFA and IgM-ELISA tests and obtained from individuals with chronic Toxoplasma infection were tested by the invention method. Negative results were obtained in all 25 sera.

EXAMPLE 3

Twenty-five sera obtained from 23 individuals with a recent history of acute toxoplasmosis and with positive titers in the DT and IgM-ELISA tests but with a negative titer in the IgM-IFA test were tested by the invention method. The results of these tests are reported in Table 1 below

TABLE 1

| Patient | DT | IgM-IFA | IgM-ELISA | Invention |
|---|---|---|---|---|
| VM | 4096 | Neg** | 256 | 1024 |
| AB | 2048 | Equivocal | 1024 | 1024 |
| BC | 4096 | Neg | 2048 | 256 |
| MD | 16000 | Neg | 256 | 1024 |
| GJ | 128 | Neg | 4 | Neg** |
| MS | 2048 | Neg | 1024 | 256 |
| GL | 8000 | Neg | 4096 | 1024 |
| KW | 8000 | Neg | 1024 | 1024 |
| CM | 256 | Neg | 1024 | Neg |
| DM | 1024 | Neg | 4 | Neg |
| AJ | 8000 | Neg | 256 | Neg |
| SK | 1024 | Neg | 16384 | 1024 |
| RR* | 8000 | Neg | 1024 | 1024 |
| RR* | 4096 | Neg | 4096 | 256 |
| CI | 8000 | Neg | 64 | Neg |
| CM | 8000 | Neg | 64 | Neg |
| DL | 1024 | Neg | 4 | 4 |
| NM* | 512 | Neg | 256 | 256 |
| NM* | 1024 | Neg | 1024 | 256 |
| FM | 4096 | Neg | 256 | 256 |
| GS | 32 | Neg | 16 | Neg |
| SL | 4096 | Neg | 256 | 256 |
| WT | 512 | Neg | 16 | 256 |
| MJ | 128 | Neg | 256 | Neg |
| BC | 128 | Neg | 128 | Neg |

*Same patient
**Neg = <16

EXAMPLE 4

Twenty-five sera obtained from 23 individuals with a recent history of acute Toxoplasma infection and with positive titers in the DT, IgM-IFA, and IgM-ELISA tests were tested by the invention method. The results of these tests are reported in Table 2 below.

TABLE 2

| Patient | DT | IgM-IFA | IgM-ELISA | Invention |
|---|---|---|---|---|
| BR | 4096 | 40 | 512 | 256 |
| KL* | 2048 | 1024 | 4096 | 4096 |
| KL* | 2048 | 256 | 1024 | 1024 |
| AS | 4096 | 256 | 256 | 1024 |
| WC | 1024 | 64 | 4096 | 4096 |
| KL | 2048 | 256 | 4096 | 1024 |

TABLE 2-continued

| Patient | Test Titer | | | |
|---|---|---|---|---|
| | DT | IgM-IFA | IgM-ELISA | Invention |
| GT | 4096 | 16 | 512 | 1024 |
| VA | 4096 | 1024 | 16384 | 4096 |
| EP | 16000 | 64 | 1024 | 256 |
| WC | 2048 | 64 | 1024 | 4096 |
| VA | 16000 | 1024 | 16384 | 4096 |
| CK | 8 | 64 | 4 | 64 |
| MD* | 32000 | 256 | 4096 | 4096 |
| MD* | 8000 | 256 | 16384 | 16384 |
| SE | 16000 | 32 | 1024 | 1024 |
| JA | 32000 | 32 | 64 | 256 |
| MH | 4096 | 20 | 2048 | 4096 |
| GM | 8000 | 64 | 16 | 256 |
| CL | 4096 | 64 | 256 | 1024 |
| JJ | 16000 | 64 | 16 | ±4 |
| KJ | 1024 | 64 | 64 | 4096 |
| AL | 1024 | 64 | 16 | 16 |
| TN | 1024 | 64 | 1024 | 4096 |
| RG | 2048 | 8 | 16 | ±4 |
| CK | 128 | 64 | 16 | 1024 |

*Same patient.

EXAMPLE 5

Eighteen sera obtained from 18 individuals with rheumatoid arthritis or systemic lupus erythematosis and with positive reactions for RF or for FANA or for both RF and FANA were tested by the DT, IgM-IFA, IgM-ELISA and invention tests. The results of these tests are reported in Table 3 below.

TABLE 3

| | | | Test Titers | | | |
|---|---|---|---|---|---|---|
| Patient | FANA | RF-Latex | DT | IgM-IFA | IgM-ELISA | Invention |
| MD | 64 | 2560 | Neg* | Neg** | Neg* | Neg** |
| OC | 256 | 5120 | Neg | Neg | Neg | Neg |
| RG | 64 | 10240 | Neg | Neg | Neg | Neg |
| SA | 64 | 20480 | Neg | Neg | Neg | Neg |
| DE | 256 | 80 | Neg | Neg | Neg | Neg |
| GM | 64 | Neg# | Neg | Neg | Neg | Neg |
| TM | 256 | Neg | 32 | Neg | Neg | Neg |
| EJ | 64 | Neg | 256 | Neg | Neg | Neg |
| MP | 256 | Neg | Neg | Neg | Neg | Neg |
| LK | 64 | Neg | Neg | Neg | Neg | Neg |
| TG | Neg | Pos## | 128 | 256 ± | Neg | Neg |
| VH | Neg | Pos | 512 | 64 ± | Neg | Neg |
| PR | Neg | Pos | 1024 | 32 | Neg | Neg |
| BC | Neg | Pos | 256 | 32 | Neg | Neg |
| HJ | Neg | Pos | 64 | 32 | Neg | Neg |
| MM | Pos | Pos | 512 | 256 ± | Neg | Neg |
| FE | Neg | 1280 | 64 | 32 | Neg | Neg |
| EM | Neg | 640 | 128 | 32 | Neg | Neg |

*Neg = <4
**Neg = <16
Negative after absorption of sera with latex particles coated with human IgG.
Neg = <20
Pos = ≧20

The results reported in Tables 1 and 2 show that the invention assay has better sensitivity than the IgM-IFA test and sensitivity comparable to the IgM-ELISA test when used to detect antitoxoplasma IgM in sera from individuals with acute acquired toxoplasmosis. The specificity of the test is evidenced by the results of Examples 1 and 2 and by the results reported in Table 3. In this regard the presence of RF and/or FANA in sera often leads to false positive results in the IgM-IFA test. As reported in Table 3, the specificity of the invention assay is not affected by the presence of RF or FANA in the serum.

EXAMPLE 6

Twelve sera from patients with acute congenital *Toxoplasma gondii* infection, two of which were negative in the IgM-IFA, were also tested by the IgM-ELISA and the invention method. The results of these tests are reported in Table 4 below.

TABLE 4

| | Test Titer | | |
|---|---|---|---|
| Patient ID No | IgM-IFA* | IgM-ELISA | Invention |
| 31 | Pos | 1024 | 64 |
| 36 | Pos | 64 | 64 |
| 40 | Neg | 1024 | 256 |
| 39 | Neg | 64 | 64 |
| 45 | Neg | 4096 | 16 |
| 34 | Neg | Neg | Neg |
| 44 | Neg | 64 | 64 |
| 32 | Neg | 1024 | 64 |
| 47 | Neg | Neg | Neg |
| 49 | Neg | 1024 | 256 |
| 50 | Neg | 64 | 64 |
| 46 | Neg | 256 | 16 |

*Pos = ≦50

The results reported in Table 4 show the increased sensitivity of the invention method as compared to the IgM-IFA test and that the invention test is of comparable sensitivity to the IgM-ELISA test for congenital forms of Toxoplasma infection.

EXAMPLE 7

This example illustrates the use of *T. gondii* antigen-coated latex particles as the antigen reagent in the assay. The following materials and methods were used. Unless indicated otherwise dilutions are by volume.

Antigen Preparation

*Toxoplasma gondii* organisms were washed with PBS and sonicated. The sonicate was centrifuged at 15,600×g for 5–10 min and the supernatant was recovered. A protein determination of the supernatant was made.

Two hundred μl of an aqueous suspension of polystyrene latex particles (Sigma, 10% solids, 1.091 micron diameter), 0.2 ml of ammonium buffer (containing $NH_4Cl$, NaCl, $NH_4OH$, 0.2M, pH 8.2) and the antigen supernatant at 25 μg protein/mg latex particles were mixed and incubated at 37° C. for 1 hr. A 0.4 ml portion of 50% sucrose in ammonium buffer was then added and the resulting mixture was incubated overnight at 4° C. The mixture was then washed twice by centrifuging at 15,600×g for 7 minutes with 1.5 ml of 5% calf serum in ammonium buffer per wash. The antigen-coated particles were resuspended in 1.5 ml of 5% calf serum in ammonium buffer. The coated latex particles were diluted 1:225 or 1:456 in alkaline buffer (7.02 g NaCl, 3.09 g $H_3BO_3$, 24 ml in NaOH, 4 g BSA, 0.1% $NaN_2$ for 1 L, pH 8.7) and used in the test.

Antihuman IgM Antibody

Affinity purified goat antihuman IgM (μ-chain specific) antibody (Tago Code 4102, Burlingame, CA.) was used. The antibody was diluted at 1:2000 in 0.1M carbonate buffer (pH 9.8).

Human Sera

The positive serum was a human serum sample that was positive in the IgM-ELISA (titer 1:16384) and in the DT (titer 1:8192). The negative serum was a pool of human sera that were negative in both the IgM-ELISa and the DT (titer < 1:64).

Method

The wells of polystyrene microtiter plates (Dynatech Laboratories, Inc.) were coated with 100 μl/well of the antihuman IgM antibody solution and incubated overnight at 4° C. The plates were then washed three times with PBS-T for five minutes each wash. Plates were postcoated with 5% DT negative calf serum in PBS-T and incubated overnight at 4° C. The plates were then washed three times in PBS-T for five minutes each wash. Following the wash 150 μl PBS was added to each well. Fifty μl of positive serum (prediluted 1:64 in PBS) and 50 μl of negative serum (prediluted 1:16) were added. Serial 4-fold dilutions (50 μl of serum + 150 μl PBS) of the negative and positive sera were made across the plate. The plate was incubated for 1 h at 37° C. followed by two washes with PBS-T and two washes with PBS. 100 μl of the antigen preparation represented by the coated latex particles were then added to each well of the microtiter plate and the plate incubated overnight at 37° C. The reaction was read visually according to the folowing criteria:

+ = button or pellet in well
− = even mat (latex distributed over wetted surface of well)
± = small pellet with some mat visible.

The results of this testing appear in Table 5 below. The designation "ND" indicates that the assay was not done.

TABLE 5

| Serum Dilution | Positive Serum 1:456* | Negative Serum 1:456* | Positive Serum 1:225* | Negative Serum 1:225* |
|---|---|---|---|---|
| 1:16 | ND | + | ND | ND |
| 1:64 | ND | + | ND | − |
| 1:256 | + | − | + | − |
| 1:1024 | + | − | + | − |
| 1:4096 | + | − | + | − |
| 1:16384 | + | − | + | − |
| 1:65536 | + | − | ± | − |
| 1:262144 | ± | − | − | − |
| 1:1048576 | − | − | − | − |
| 1:4194304 | − | − | − | − |
| 1:16777216 | − | − | − | − |
| 1:167108864 | − | ND | − | − |
| 1:27 × 10$^8$ | − | ND | − | − |
| No Serum | − | − | − | − |

*Dilutions of latex.

These results indicate that the level of antigen dilution affects the sensitivity of the assay using antigen-coated latex.

EXAMPLE 8

A modification of the assay procedure described in Example 7 in which a single dilution of serum was allowed to react with three different concentrations of the antigen-coated latex particles was also carried out. This modification was tried to determine whether a single dilution of the test serum would be sufficient to allow for the detection of specific antitoxoplasma IgM and the establish a diagnosis of acute toxoplasmosis. The coating of the plates was as described in Example 7. The final dilution of the test sera in three different wells was 1:100. Following incubation for one hr at 37° C., the sera were removed and the wells washed as in Example 7. Without allowing the plates to dry, 100, 140, or 200 μl of antigen-coated latex particles were added to the individual wells. The plates were agitated for one min and incubated at 37° C. for one hr. Thereafter, the plate was centrifuged at 3000 rpm for 10 min at room temperature and allowed to settle for 90 min. After this period of time, a first reading was performed and the plates kept overnight at room temperature for a further second reading. This was done to determine whether a reading after 5 hours of initiation of the test would be feasible and comparable to a regular reading performed after overnight incubation. The reading was performed by comparing each well with a given concentration of latex particles with its negative control. The results were recorded as: (a) a complete mat of latex particles = 4; (b) a mat with a small button = 3; (c) a mat with an intermediate button = 2; (d) a button slightly smaller than the respective negative control = 1; (e) a well-defined button = 0. The numbers obtained in each well were added and the sum varied from 0 (all three wells negative) to 12 (all three wells strongly positive). This procedure was carried out on sera from eight patients. For comparison purposes the sera were also assayed by the procedure of Example 7 and the the IgM-ELISA test. The results of these tests are reported in Table 6 below.

TABLE 6

| Patient serum | Example 8 Results 5 hour | Example 8 Results overnight | Example 7 Results* | IgM-ELISA Results |
|---|---|---|---|---|
| D1 | 12 | 12 | 11,11 | 9.7 |
| D2 | 11 | 12 | 11,11 | 10.4 |
| D5 | 0 | 0 | 0,0 | 0 |
| D6 | 6 | 4 | 3,3 | 4.0 |
| D11 | 7 | 4 | 5,3 | 7.0 |
| D12 | 8 | 7 | 10,9 | 7.3 |
| D13 | 8 | 7 | 9,7 | 6.6 |
| D16 | 0 | 3 | 0,0 | 0.5 |
| Pos. control | 11 | 12 | 11,11 | 11.0 |
| Neg. control | 0 | 0 | ND | ND |

*Two readings.

EXAMPLE 9

This example illustrates the use of antigen-coated turkey red blood cells as the antigen reagent in the assay. The following materials and methods were used. Unless indicated otherwise dilutions are by volume.

Antigen Preparation

Formalinised, tanned turkey red blood cells coated with sonicate of *T. gondii* from the ToxHA test kit (Wellcome Laboratories, Research Triangle Park, N.C.) was used. The kit buffer diluent is PBS (pH 7.2) containing 1.5% normal rabbit serum and 0.1% NaN$_2$.

Antihuman IgM Antibody

The antibody preparation of Example 7 was used.

Human Sera

The positive and negative sera of Example 7 were used.

Method

The V-shaped wells of polystyrene microtiter plates (Dynatech Laboratories, Inc.) were coated with antihuman IgM antibody, incubated and washed, post-coated with 5% calf serum, and incubated and washed as in Example 7. One-hundred fifty μl PBS was added to each well. To the wells in the first column in the plate 50 μl of positive serum prediluted 1:64 in PBS was added. A serial 4-fold dilution was done by transferring 50 μl to subsequent wells through column 6. Negative serum prediluted 1:4 in PBS was serially diluted in columns 7-10. No serum was added to columns 11 and 12. The plate was incubated 1 h at 37° C. and then washed twice with PBS-T and twice with PBS. The antigen preparation was then added at various dilutions in the kit buffer at 100 μl/well. The plate was incubated at 37° C. for 1 h and then overnight at room temperature. Readings were made as in Example 7. Control tests were run using formalinised, tanned turkey red blood cells not coated with *T. gondii* antigen. The results of these tests are reported in Table 7 below.

TABLE 7

| | | Red-blood cells* | | | | | | | |
|---|---|---|---|---|---|---|---|---|---|
| | | Coated and Diluted+ | | | | Uncoated and diluted+ | | | |
| Serum | Dilution | 64 | 128 | 256 | 512 | 64 | 128 | 256 | 512 |
| Positive | 1:256 | + | + | + | + | − | − | − | + |
| | 1:1024 | + | + | + | + | − | − | − | ± |
| | 1:4096 | ± | + | ± | + | − | − | − | + |
| | 1:16384 | − | ± | ± | + | − | − | − | ± |
| | 1:65536 | − | − | ± | + | − | − | − | ± |
| | 1:262144 | − | − | ± | + | − | − | − | ± |
| Negative | 1:16 | − | − | ± | + | − | − | − | + |
| | 1:64 | − | − | ± | + | − | − | − | + |
| | 1:256 | − | − | ± | + | − | − | − | + |
| | 1:1024 | − | − | + | + | − | − | − | + |
| No serum | | − | − | − | + | − | − | − | + |

*Coated or uncoated with *T. gondii* antigen
+Dilutions are the reciprocal of the dilution of the red blood cell suspension in the supplier's kit.

These results indicate that the concentration of antigen represented by the coated RBC used is important. The best dilution of these cells to be used in the test was 1:128 since the highest titer with the positive serum and a totally negative result with the negative serum was retained with this dilution. When the coated RBC were diluted 1:256 or 1:512 undefined or false positive results were noted including the well in which serum either positive or negative was absent. The importance of using the proper dilution of cells is emphasized by the fact that uncoated cells diluted 1:512 yielded undefined results with the positive serum or false positive results with the negative serum.

The above described modes for carrying out the invention relate particularly to detecting IgM associated with acute forms of *Toxoplasma gondii* infection in humans. Asay for detecting Ig antibodies associated with conditions other than acute *Toxoplasma gondii* infection such as IgM associated with hepatitis A, rubella, polio, herpes simplex, cytomegalo virus, Epstein-Barr virus, and various fungi, protozoa, and helminths in the serum or other body fluids of human and other species of the Animalia kingdom may be carried out in a similar manner using the invention method. The invention may also be used to detect specific classes of Ig other than IgM such as IgG, IgA, IgE, and IgD and the subclasses thereof in the serum or other body fluids of humans and other species of the Animalia kingdom. In such other embodiments of the invention it may be necessary to use different temperatures, pHs, and concentrations than are used to assay for human antitoxoplasm IgM to obtain optimum results.

The test kits for carrying out the immunoassay will contain as basic ingredients given amounts of the antibody against the Ig and the insoluble, nontranslucent form of antigen. These ingredients are dispensed in suitable containers. The kit will also typically include diluents for the reagents and samples, a postcoating preparation, and directions for performing the method. The kit components may be packaged in manners conventional in the immunodiagnostic kit art.

Modifications of the above described modes for carrying out the invention that are obvious to those of skill in immunology and/or related arts are intended to be within the scope of the following claims.

We claim:
1. An immunoassay for detecting in a sample of body fluid an Ig that binds specifically to an antigen associated with a microorganism comprising the steps of:
   (a) adsorbing an antibody against said Ig onto the solid surface of a well-shaped container;
   (b) applying the sample to the adsorbed antibody against said Ig and incubating the resulting mixture;
   (c) separating the nonadsorbed fraction from the adsorbed fraction of the incubated mixture of step (b);
   (d) applying the microorganism as constituting an insoluble, opaque, directly observable form of the antigen to the adsorbed fraction; and
   (e) observing directly the extent to which the insoluble opaque antigen is bound to the adsorbed fraction by observing the distribution of the antigen on the wall of the container.

2. The immunoassay of claim 1 wherein the body fluid is a human body fluid.

3. The immunoassay of claim 1 wherein the antigen is an antigen that is associated with a human disease.

4. The immunoassay of claim 1 wherein the antigen is an antigen that is associated with *Toxoplasma gondii*.

5. A test kit for carrying out the immunoassay of claim 1 comprising, separately provided:
   (a) an antibody against the Ig; and
   (b) a preparation of whole microorganisms as constituting an insoluble, opaque, directly observable form of the antigen.

6. The immunoassay of claim 1 wherein the Ig is a specific class of Ig.

7. The immunoassay of claim 6 wherein the body fluid is a human body fluid.

8. A test kit for carrying out the immunoassay of claim 6 comprising separately provided:
   (a) an antibody against the Ig; and
   (b) a preparation of whole microorganisms as constituting an insoluble opaque form of the antigen.

9. The immunoassay of claim 1 wherein the Ig is IgM.

10. The immunoassay of claim 9 wherein the body fluid is a human body fluid.

11. A test kit for carrying out the immunoassay of claim 9 comprising separately provided:
   (a) an antibody against the Ig; and
   (b) a preparation of whole microorganisms as constituting an insoluble opaque nontranslucent form of the antigen.

12. An immunoassay for detecting IgM associated with an acute form of *Toxoplasma gondii* infection in a sample of human body fluid comprising the steps of:
   (a) adsorbing antihuman IgM antibody onto the solid surface of a well-shaped container;
   (b) applying the sample to the adsorbed antihuman IgM antibody and incubating the resulting mixture;
   (c) separating the nonadsorbed fraction from the adsorbed fraction of the incubated mixture;
   (d) applying a preparation of whole *Toxoplasma gondii* organisms as constituting an insoluble, opaque, directly observable form of *Toxoplasma gondii* antigen to the adsorbed fraction at a basic pH and incubating the resulting mixture; and (e) observing directly the extent to which the antigen is bound to the antigen on the wall of the container.

13. The immunoassay of claim 13 wherein between steps (a) and (b) the surface is post-coated with an appropriate protein.

14. The immunoassay of claim 12 wherein the pH is 8.2 to 8.7, inclusive.

15. A test kit for carrying out the immunoassay of claim 12 comprising, separately provided (a) antihuman IgM antibody; and (b) a preparation of whole *Toxoplasma gondii* organisms which constitutes an insolubilized, opaque, directly observable form of *Toxoplasma gondii* antigen.

16. An immunoassay for detecting, in a sample of body fluid, an Ig that binds specifically to an antigen comprising the steps of:

(a) adsorbing an antibody against said Ig and specific for the class of the Ig onto the solid surface of a well-shaped container;

(b) applying the sample to the adsorbed antibody against said Ig and incubating the resulting mixture;

(c) separating the nonadsorbed fraction from the adsorbed fraction of the incubated mixture of step (b);

(d) applying an insoluble, opaque, directly observable form of the antigen to the adsorbed fraction; and (e) observing directly the extent to which the insoluble, opaque antigen is bound to the adsorbed fraction by observing the distribution of the antigen on the wall of the container.

17. The immunoassay of claim 16 wherein the insoluble, opaque directly observable form of the antigen is a whole organism or antigen fixed to the surface of a particulate carrier.

18. The immunoassay of claim 17 wherein the insoluble, opaque, directly observable form of the antigen is a whole microorganism.

19. The immunoassay of claim 18 wherein the whole microorganism is *Toxoplasma gondii*.

20. The immunoassay of claim 16 wherein the Ig is IgM.

21. A test kit for carrying out the immunoassay of claim 20 comprising, separately provided (a) antihuman IgM antibody; and (b) an insolubilized, opaque, directly observable form of antigen.

22. The test kit of claim 21 wherein the insoluble, opaque, directly observable form of the antigen is a preparation of whole microorganisms.

* * * * *